United States Patent
Geurts (10) Patent No.: US 11,958,792 B2
(45) Date of Patent: Apr. 16, 2024

(54) THERMAL STRIPPING UREA PLANT AND PROCESS

(71) Applicant: STAMICARBON B.V., Sittard (NL)

(72) Inventor: Wilhelmus Hubertus Geurts, Sittard (NL)

(73) Assignee: Stamicarbon B.V., Sittard (NL)

( * ) Notice: Subject to any disclaimer, the term of this patent is extended or adjusted under 35 U.S.C. 154(b) by 0 days.

(21) Appl. No.: 18/447,469

(22) Filed: Aug. 10, 2023

(65) Prior Publication Data

US 2023/0382849 A1    Nov. 30, 2023

Related U.S. Application Data

(62) Division of application No. 17/636,257, filed as application No. PCT/NL2021/050395 on Jun. 23, 2021.

(30) Foreign Application Priority Data

Jun. 23, 2020    (EP) .................................... 20181754

(51) Int. Cl.
| | | |
|---|---|---|
| C07C 273/04 | (2006.01) | |
| B01D 5/00 | (2006.01) | |
| B01J 3/02 | (2006.01) | |
| B01J 3/04 | (2006.01) | |

(52) U.S. Cl.
CPC .......... *C07C 273/04* (2013.01); *B01D 5/0075* (2013.01); *B01J 3/02* (2013.01); *B01J 3/042* (2013.01)

(58) Field of Classification Search
CPC ........ C07C 273/04; B01D 5/0075; B01J 3/02; B01J 3/042
See application file for complete search history.

(56) References Cited

U.S. PATENT DOCUMENTS

| | | |
|---|---|---|
| 5,681,537 A | 10/1997 | Pagani |
| 6,852,886 B2 | 2/2005 | Mennen |
| 2004/0116743 A1 | 6/2004 | Mennen |
| 2008/0118414 A1 | 5/2008 | Pagani |
| 2009/0124830 A1 | 5/2009 | Zardi et al. |
| 2010/0063321 A1 | 3/2010 | Zardi et al. |
| 2012/0302789 A1 | 11/2012 | Mennen |
| 2015/0025273 A1 | 1/2015 | Carlessi et al. |
| 2015/0322000 A1 | 11/2015 | Buitink et al. |
| 2020/0190023 A1 | 6/2020 | Bertini et al. |

FOREIGN PATENT DOCUMENTS

| | | |
|---|---|---|
| EP | 0598250 A1 | 5/1994 |
| EP | 2707355 B1 | 6/2016 |
| WO | 2017014632 A1 | 1/2017 |

OTHER PUBLICATIONS

Jozef H. Meessen, Chapter Urea, in Ullmann's Encyclopedia of Industrial Chemistry, edition 2010. 39 pages.

(Continued)

*Primary Examiner* — Renee Robinson
(74) *Attorney, Agent, or Firm* — Leason Ellis LLP (57) ABSTRACT

The disclosure pertains to a urea production plant and process using a thermal stripper, wherein the reaction mixture is separated in two parts, wherein the first part is supplied at least in part to the thermal stripper and the second part at least in part bypasses the thermal stripper and is supplied to a medium pressure recovery section.

7 Claims, 2 Drawing Sheets

(56) References Cited

OTHER PUBLICATIONS

W.A.G. Lemmen, "Environmental Impact of Stamicarbon 2,000-MTPD Urea Plant", Stamicarbon BV, Geleen, The Netherlands. 1993, 9, pages.

International Search Report and Written Opinion in corresponding International Patent Application No. PCT/NL2021/050395 dated Sep. 21, 2021.

THERMAL STRIPPING UREA PLANT AND PROCESS

CROSS-REFERENCE TO RELATED PATENT APPLICATIONS

This application is a divisional application of U.S. application Ser. No. 17/636,257, filed on Feb. 17, 2022, which is a U.S. National Stage Application under 35 U.S.C. § 371 of International Patent Application No. PCT/NL2021/050395, filed Jun. 23, 2021, which claims the benefit of priority of European Patent Application No. 20181754.1 filed Jun. 23, 2020, both of which are incorporated by reference in their entireties. The International Application was published on Dec. 30, 2021, as International Publication No. WO 2021/261999 A1.

FIELD

The invention pertains to the production of urea and in particular to a urea plant and process using a high pressure stripper of the thermal stripping type (also known as the self-stripping type).

INTRODUCTION

The invention pertains to the production of urea from $NH_3$ and $CO_2$ feed in a high pressure reaction zone. The synthesis stream from the reaction zone contains urea, water, ammonium carbamate, ammonia (partly in the gas phase) and inert gases. The synthesis stream needs to be purified into a urea product in the urea plant and process.

The inert gases originate from the $NH_3$ feed and $CO_2$ feed; the inert gases e.g. include $H_2$. The $NH_3$ feed in some embodiments contain some $CH_4$. In numerous existing urea plants, passivation air is added to the $CO_2$ feed, this air is also comprised in the 'inerts'. Oxygen in passivation air is used to prevent corrosion of high pressure (HP) equipment parts of urea plants.

Urea production plants are often of the 'total recycle type'. In such plants, the urea synthesis stream from the high pressure reaction zone which contains urea, water, ammonia, and ammonium carbamate is expanded and subjected to decomposition of the carbamate to give a purified urea solution and a gas stream containing $NH_3$ and $CO_2$. The gas stream is subjected to condensation to form a carbamate solution which solution is pumped back to the high pressure reaction zone. This recycled carbamate solution contains water to avoid the solidification of ammonium carbamate. As water is a by-product in the urea formation reaction, the recycle of water is undesirable and it is desired to minimize the water content of the carbamate recycle stream. It is generally desired to minimize the specific water amount introduced into the HP reaction zone from the low and medium pressure sections.

Urea processes of the stripping-type are based on the total recycle design and use a high pressure stripper. The present invention generally pertains to a urea production process of the stripping type. In a stripping-type urea production process, the synthesis stream from the reactor is subjected at least in part, such as entirely, to stripping at high pressure in the stripper to decompose the ammonium carbamate into a gas stream containing $NH_3$ and $CO_2$. The stripper operates for instance at substantially the same pressure as the reactor. Said gas stream leaving the stripper is condensed in the high pressure carbamate condenser (HPCC). High pressure stripping in urea plants generally involves heating the urea synthesis solution and contacting the liquid with a gas stream in counter-current flow wherein the gas stream has a lower partial vapor pressure of $NH_3$ and/or $CO_2$ than the liquid to provide for a stripping effect.

In urea processes of the stripping type, the HP stripper and the HP carbamate condenser are each typically shell-and-tube heat exchangers with a tube bundle that contains thousands of tubes. The HP reactor is often a vertical vessel with trays. The stripper is typically a falling-film shell-and-tube heat exchanger with urea solution in the tubes and strip-gas flowing up. The HP carbamate condenser is typically a shell-and-tube heat exchanger with a horizontal or vertical tube bundle, with straight or U-shaped tubes, and with cooling fluid or process medium (process fluids) in the tubes.

In plants of the $CO_2$ stripping type, the strip gas is $CO_2$ feed; the N/C ratio in the reactor is about 3.0 and the N/C ratio of the stripped urea solution is relatively low. In plants of the $CO_2$ stripping type, the HP reactor typically has separate outlets for inert gases sent to a HP scrubber and for urea synthesis solution sent to the HP stripper.

The present invention is directed to urea process of the thermal stripping type (also known as 'self-stripping' type). In plants of the thermal stripping type the urea reactor operates at a relatively high N/C ratio of above 3.0, in plants of the 'Snamprogetti' design often at N/C ratio of 3.2-3.6, e.g. 3.2-3.4. The reactor is operated at e.g. 150 to 160 bar.

The urea synthesis stream supplied to a thermal stripper is therefore relatively rich in $NH_3$ and the strip gas is provided by the heating (or reboiling) of the liquid at a downstream part of the HP thermal stripper to form a gas stream rich in $NH_3$ which is in counter-current contact with the incoming urea synthesis stream thereby providing for a stripping effect. A thermal stripper does not receive $CO_2$ feed as strip gas. The thermal stripper may optionally receive some passivation air at the bottom in some embodiments.

The stripped urea solution from a thermal stripper has a relatively high N/C ratio and is supplied to a medium pressure (MP) recovery section comprising an MP decomposer, a MP carbamate condenser and a separate MP ammonia condenser. The MP decomposer gives urea solution that is sent to the LP recovery section and a gas stream containing $CO_2$ and relatively high amounts of $NH_3$. The gas stream is subjected to condensation in the MP carbamate condenser to give carbamate solution and remaining $NH_3$ gas. The remaining $NH_3$ gas from the MP condenser is subjected to condensation in the MP ammonia condenser. Condensed ammonia and carbamate solution are separately pumped back from the MP section to the HP section, typically as two different liquid streams with different temperatures and using different pumps.

An example urea process of the thermal stripping type is the 'Snamprogetti' urea process illustrated in Ullmann's Encyclopaedia of Industrial Chemistry, Chapter Urea, 2010, FIG. 25. In the illustrative process of that figure, the high pressure (HP) reactor has one outlet and the entire urea synthesis stream from the reactor is supplied to the HP stripper which is of the thermal stripping type. The inert gases pass through the HPCC, whereby oxygen comprised in the inert gases provides for corrosion protection of the HPCC, and the inert gases are separated from the HP condensate in a HP carbamate separator and supplied as gas stream to the MP recovery section where they are vented from an ammonia scrubber arranged downstream of the ammonia condenser. In this way, the vented inert gases do not contain much $NH_3$ despite the relatively high N/C ratio of the urea solution in the thermal stripper. The MP recovery section typically operates at 18 bar in the 'Snamprogetti' design.

There is a desire for large scale urea plants wherein advantageously the high pressure stripper and the high pressure condenser are relatively small compared to the plant capacity. This avoids the disadvantage of the stripper and condenser (typically shell-and-tube heat exchangers) becoming very heavy and bulky and difficult to transport for construction of the plant, such as in case of newly-built plant ('grassroots plant'). Furthermore, there is a desire to increase the capacity of existing urea plants of the thermal stripping type (so-called 'revamping') without having to modify the HP stripper and condenser or without having to add a HP stripper or condenser.

US 2004/0116743A1 mentions that the HP stripping step and the HP condensation step are largely responsible for the fact that it is only to a limited extent possible to expand the capacity of an existing facility without modification or replacement of expensive high-pressure equipment. U.S. Pat. No. '743 proposes increasing the capacity of a plant by modifying the plant such that a part of the urea synthesis solution is transferred from the synthesis zone to a medium-pressure treatment zone operated at a pressure of 1-4 MPa; the other part is sent to the HP stripper. U.S. Pat. No. '743 illustrates the design for HP strippers of the $CO_2$ type, but mentions that use may also be made of thermal stripping. However, no details are given of that embodiment and in FIGS. 2 and 4 of U.S. Pat. No. '743, a $CO_2$ stripper is used and the inert gas stream 'RG' is sent from the top of the reactor to a scrubber. This is not desirable in case of a thermal HP stripper due to the higher N/C ratio.

There remains a desire for improved urea process and plants of the thermal stripping type, such as with a relatively large capacity and low water recycle, and for corresponding revamping methods.

SUMMARY

The invention pertains in a first aspect to a urea production process carried out in a urea production plant of the thermal stripping type, the plant comprising a high pressure (HP) synthesis section and a first and a second medium pressure (MP) recovery section, wherein the HP synthesis section comprises a HP reaction zone, a HP stripper of the thermal stripping type, and a HP carbamate condenser, wherein the HP stripper has an outlet for stripped urea solution connected to the first MP recovery section and an outlet for gas connected to the HP carbamate condenser, wherein the HP synthesis section further comprises a separator, the process comprising: separating the reaction mixture from the reaction zone at high pressure in said separator into first stream, e.g. an ammonia-rich first stream, and a second stream, wherein the first stream and the second stream both contain a liquid phase containing urea, wherein the first stream (e.g. ammonia-rich first stream) preferably has a lower gravimetric density than the second stream, wherein the first stream (e g ammonia-rich first stream) preferably has a higher concentration of ammonia than the second stream; supplying the first stream (e.g. ammonia-rich first stream) at least in part (e.g. entirely) to the stripper; and supplying the second stream at least in part (e.g. entirely) to the second medium pressure recovery section. Preferably the first stream has a lower gravimetric density than the second stream and the first stream is an ammonia-rich first stream having a higher concentration of ammonia than the second stream; and/or preferably the second stream is expanded from high pressure to medium pressure in a MP adiabatic flashing unit comprised in the second MP recovery section thereby obtaining a gaseous stream and a flashed MP urea solution.

The invention also pertains to a urea plant, preferably suitable for the inventive urea production process as described herein, the plant comprising a high pressure synthesis section comprising a reaction zone, a thermal stripper, and a carbamate condenser, the plant further comprising a first medium pressure recovery section having an inlet connected to an outlet for stripped urea solution of said thermal stripper, wherein the high pressure section comprises a high pressure separator configured for separating a high pressure reaction mixture from the reaction zone into a first stream and a second stream, the first stream and the second stream both containing a liquid phase containing urea and the first stream preferably having a lower gravimetric density than the second stream; and wherein the high pressure separator has a first outlet for the first stream connected to an inlet of said thermal stripper, and a second outlet for the second stream connected to a second medium pressure recovery section.

The invention also pertains to a method of modifying an existing urea plant of the thermal stripping type, preferably into an inventive plant as described herein, wherein the existing plant comprises a high pressure synthesis section comprising a reaction zone, a thermal stripper, and a carbamate condenser, the existing plant further comprising a first medium pressure recovery section having an inlet connected to an outlet for stripped urea solution of said thermal stripper, the method comprising: adding a high pressure separator to the high pressure synthesis section configured for separating a high pressure reaction mixture from the reaction zone into a first stream and a second stream, the first stream and the second stream both containing a liquid phase containing urea and the first stream preferably having a lower gravimetric density than the second stream; and adding a second medium pressure (MP) recovery section, wherein the high pressure separator has a first outlet for the first stream connected to an inlet of said thermal stripper, and a second outlet for the second stream connected to said second medium pressure recovery section.

Any embodiments illustrated in the figures are examples only and do not limit the invention.

DETAILED DESCRIPTION

Embodiments of the present invention are broadly based on the judicious insight to separate the urea synthesis stream from the reaction zone in a high pressure separator into a first stream and a second stream both containing a liquid phase and both containing urea, wherein the first stream is preferably more ammonia-rich than the second stream.

In some embodiments of the invention, the ammonia-rich first fluid stream from the high pressure separator has a higher concentration of ammonia than the second fluid stream from the high pressure separator, wherein the ammonia concentration is based on both gas and liquid together for two phase fluid streams.

In some embodiments, the second stream may have a lower, higher, or the same $NH_3$ concentration than the first stream.

Preferably, a flashing step and/or N/C measurement is used for the second stream.

Preferably the process involves determining the N/C ratio of the second stream. Determining the N/C ratio is advantageously in particular simple in preferred embodiments wherein the second stream consists of degassed liquid. Very advantageously in these embodiments with a degassed second stream consists of liquid, instead of a two-phase gas/liquid fluid stream, and the N/C ratio can accordingly be conveniently measured.

In a highly preferred embodiment, the second stream is subjected to adiabatic flashing and the formed flash vapor is supplied directly or indirectly to an ammonia condenser to form ammonia condensate which is recycled to the HP synthesis section. Thereby advantageously essentially water-free recycle of the ammonia condensate is achieved while at the same time a low water content of the carbamate recycle stream from the second MP recovery section is obtained.

Preferably the flash vapor is supplied to the first MP recovery section, in particular directly or indirectly to an ammonia condenser of the first MP recovery section, to condense as ammonia condensate which is recycled to the synthesis section using an ammonia pump. Thereby advantageously use is made of the equipment in the first MP recovery section.

The first stream preferably comprises both vapor and liquid and preferably is a two-phase fluid. The second stream preferably consists essentially of liquid. Preferably, the separation involves degassing the second stream. The first stream (total stream, including both gas and liquid in case of a two-phase fluid) has a higher ammonia concentration than the second stream. Such separation can be done at high pressure based on e.g. gravimetric density separation.

The ammonia-rich first stream preferably has a lower gravimetric density than the second stream. This refers to the gravimetric density of the entire stream (gas and liquid together in case of two-phase fluid streams), and the density at the separation step and/or inside the separator. The density of the streams may increase or decrease downstream of the separation step.

In a preferred embodiment, the separator comprises a funnel, with a downward liquid outlet at the narrow opening of the funnel, preferably for the second stream and alternatively for the first stream. Preferably, the separator comprises a funnel having a bottom and top and a narrow opening at the bottom and a wide opening at the top, wherein the narrow opening is connected to the outlet for the second stream of the separator. Preferably, the surface area of the wide opening is at least 2× or at least 4× the surface area of the narrow opening of the funnel. Herein, top and bottom refer to gravity. Additionally, the funnel is preferably arranged in the top part of a vertical urea reactor. The urea reactor has at the bottom an inlet connected directly or indirectly to an outlet of the HP carbamate condenser for receiving liquid from the HP carbamate condenser.

The funnel structure is e.g. conically tapered with a wide opening and a narrow opening. Preferably, the funnel is in operation completely submerged in the reaction mixture phase that comprises urea solution. The reaction mixture flows relatively slowly downward in the funnel and becomes degassed urea solution that is withdrawn as preferably the second stream or alternatively the first stream. A wide funnel (at the wide opening) leads to a low downward velocity of the liquid inside the funnel which allows the liquid to degas. The funnel outlet (narrow opening) is e.g. connected to a downcomer.

Preferably the process involves degassing the second stream in the HP separator. Preferably the process involves supplying the degassed second stream to the second MP recovery section, preferably with bypassing of the thermal stripper, such that the second MP recovery section receives degassed non-stripped urea synthesis solution. Preferably the process involves determining the N/C ratio of the degassed second stream.

In another embodiment, the first stream is degassed in the HP separator, and the degassed first stream is supplied to the thermal stripper. Preferably in this embodiment, the process involves determining the N/C ratio of the first stream.

Preferably, the first and the second stream have a different composition already directly after the separation. Preferably, the first and the second stream have a different composition at high pressure, prior to any expansion step to lower pressure. Preferably, the first and the second stream have a different composition at the outlets of the separator, and have a pressure at the outlets of the separator that is the same as the operating pressure of the reactor or that is less than 10 bar lower than said operating pressure of the reactor.

Such embodiments of the present disclosure fundamentally depart from US 2004/0116743A1 wherein the first part of the synthesis solution sent to the stripper and the second part sent to the MP section have the same composition (before the expansion of the second part from HP to MP).

In other less preferred embodiments, the first and second stream have the same composition, as in US 2004/0116743A1, for instance if no N/C meter is used.

The two streams from the HP separation step are at least in part, such as entirely, subjected to different treatments in the invention, in particular the streams are at least in part, such as entirely, supplied to different units. The processing of the two streams can be adapted to the specific composition of each stream.

The first stream is at least in part, such as entirely, e.g. for at least 90 wt. % of the liquid phase, sent to the HP stripper of the thermal stripping type. The stripped urea solution from the thermal stripper is at least in part, such as entirely, such as for at least wt. %, sent to the first MP recovery section.

The first MP recovery section preferably comprises a MP decomposer, a MP carbamate condenser and a MP ammonia condenser, and preferably also a MP carbamate separation column and a MP ammonia receiver. The first MP recovery section preferably has separate recycle flow connections for the condensed ammonia stream and for the first carbamate solution, for recycling these streams separately to the HP section.

In some embodiments, the first stream can be separated into sub-streams and one or more of these sub-streams are supplied at least in part, such as entirely, to the thermal stripper. For instance, if the first stream is a two-phase fluid, the first stream is e.g. subjected to gas/liquid separation and the liquid stream is e.g. supplied to the stripper and the gas stream is e.g. supplied to the high pressure carbamate condenser. In such an embodiment, only a part of the first stream is supplied to the thermal stripper.

Typically, the first stream is subjected to gas/liquid separation downstream of the HP separation step and the liquid is distributed over the tube inlets of the tube bundle of the thermal stripper. This gas/liquid separation is e.g. carried out in an upper chamber of the thermal stripper. The gas/liquid separation can also be carried out in an additional separation vessel arranged between the HP separator and the stripper, with liquid supplied to the thermal stripper and gas to the HPCC.

The gas from the gas/liquid separation, comprising inert gases and $NH_3$, is preferably sent to the HPCC, for instance mixed with the gas stream released by the stripping treatment in the tube bundle of the thermal stripper. In this way oxygen comprised in the inert gases contributes to corrosion prevention both in the reactor and in the HPCC.

Preferably, the first stream is entirely or substantially entirely (e.g. at least wt. % of the liquid phase) sent to the thermal stripper.

The second stream preferably bypasses the HP stripper and is sent at least in part, such as entirely, to a second MP recovery section, preferably the second stream is entirely or substantially entirely (e.g. at least 95 wt. %) sent to a second MP recovery section. Advantageously, the capacity of the HP stripper and the HP carbamate condenser can therefore be small relative to the capacity of the urea plant.

Preferably, the second MP recovery section receives at least 95 wt. % or at least 99 wt. % of the second stream as provided by the high pressure separator. The second MP recovery section preferably receives non-stripped urea solution from the HP reactor as said second stream.

Preferably, the second MP recovery section receives 5-50 wt. % of the urea produced in the HP synthesis section, more preferably 15-30 wt. %.

The second MP recovery section comprises a second MP decomposer, a second MP carbamate condenser, and preferably a MP adiabatic flash unit. The second MP recovery section advantageously operates independently of the first MP recovery section. This allows for using optimal process conditions in each section.

The preferred MP adiabatic flash unit receives at least a part, preferably all, of the second stream, preferably the degassed second stream, and has a first outlet for flash vapor and a second outlet for flashed urea solution. The MP flash unit is preferably adiabatic in that it is preferably not actively heated. This has the advantage that the endothermic carbamate decomposition reaction proceeds hardly or only to a limited extent such that the flash vapor has a relatively low $CO_2$ content. Furthermore, the adiabatic flash provides for low water evaporation and an advantageously low water content of the flash vapor. Preferably the flash vapor comprises at least 90 wt. % $NH_3$ or is essentially pure $NH_3$. The N/C ratio of the urea solution decreases by the flashing advantageously giving less water recycle in the carbamate from the second MP recovery section and improved urea conversion. The MP adiabatic flash unit preferably operates at a higher pressure than the second MP decomposer, preferably at least 1.0 bar higher or e.g. at least 5 bar higher or e.g. at least 10 bar higher, typically less than 30 bar higher, and preferably also at least 1.0 bar or at least 2 bar higher than the first MP recovery section. The flashed urea solution is preferably accordingly reduced in pressure between the MP adiabatic flash unit and the second MP decomposer by at least 1.0 bar, at least 5 bar or e.g. at least 10 bar.

The MP adiabatic flash unit preferably operates at a pressure of at least 20 bar (absolute), for instance at a pressure in the range of 20 to 60 bar (absolute), e.g. 25 to 40 bar, such as at 25 to 35 bar or e.g. at 30 to 40 bar. The pressure of the MP adiabatic flash step can advantageously be used to adjust the composition of the recycle carbamate streams.

The urea solution at the outlet of the MP flash unit for instance comprises 15-25 mol. % $NH_3$ (both free and as carbamate) and 5-15 mol. % $CO_2$ (both free and as carbamate), for instance at a pressure of 20-30 bar.

In an example, the urea solution as the outlet of the MP flash unit for example 23 mol. % $NH_3$ (both free and as carbamate), 10 mol. % $CO_2$ (both free and as carbamate), 19 mol. % urea and 32 mol. % water, at 25 bar and 133° C.

The flash vapor is preferably subjected to condensation to form a liquid condensate which is typically recycled to the HP section, preferably using a pump. In some embodiments a dedicated ammonia condenser is used. In a highly preferred embodiment, the vapor from the adiabatic flash is supplied to the MP carbamate condenser of the first MP recovery section. This MP carbamate condenser has a gas outlet connected to a gas flow to the ammonia condenser of the first MP recovery section. In this way, excess $NH_3$ contained in the vapor from the adiabatic flash is advantageously condensed in the ammonia condenser of the first MP recovery section as relatively pure liquid $NH_3$. By virtue of the flashing, a high N/C ratio of the second stream, for instance in embodiments with a reactor operating with N/C ratio in the range of 3.0 to 3.4, may advantageously be combined with high quality carbamate recycle solution from the second MP recovery section. Moreover the process takes benefit from the first MP recovery section downstream of the HP thermal stripper being adapted to processing stripped urea solution with relatively high N/C ratio and the essentially water-free ammonia recycle from the ammonia condenser to the HP synthesis section.

Therefore in a preferred embodiment an MP adiabatic flash unit is used which receives a part of the urea synthesis stream from the reactor (second stream) and the flash vapor is supplied to the MP carbamate condenser of the first MP recovery section. In this embodiment, but also in other embodiments, the second stream may e.g. have the same, higher, or lower gravimetric density as the first stream, and the second stream may have higher, the same, or lower $NH_3$ concentration as the first stream.

The MP adiabatic flash unit preferably operates at a higher pressure than the first MP decomposer and the first MP carbamate condenser, preferably at least 1.0 bar higher, to allow for vapor transport.

In case of a modification of an existing urea plant (revamp), the carbamate condenser and the ammonia condenser of the existing first MP recovery section usually have a margin to receive vapor from the adiabatic flash. The pressure of the adiabatic flash can be used to adjust the amount of flashed gas.

The second MP decomposer has an inlet for the preferably flashed urea solution or for the second stream (if the preferred adiabatic flash is not used), an outlet for vapor and an outlet for urea solution. The second MP decomposer comprises typically a heat exchanger, preferably comprises a shell-and-tube heat exchanger, and preferably uses steam as heating fluid. The second MP decomposer comprises e.g. a vertical straight tube shell-and-tube heat exchanger having a rectifier on top. The rectifier comprises a packing allowing for contact between incoming, downward falling liquid and the upward moving gas. The gas outlet is preferably at the top. The liquid inlet is preferably at an upper part of the rectifier. The second MP decomposer is operated e.g. at 15 to 25 bar.

The first and second MP decomposer can advantageously be operated at different pressures. The second MP decomposer is e.g. operated at a higher pressure than the first MP decomposer, e.g. at least 1.0 bar or at least 5.0 bar higher, e.g. 5 to 15 bar higher. This may contribute to a relatively high condensation temperature in the second MP carbamate condenser.

The vapor from the second MP decomposer is supplied to the second MP carbamate condenser which has an outlet for carbamate solution. The second MP carbamate condenser may be provided as one or more units. For instance, it is provided as two shell-and-tube heat exchangers. The second MPCC comprises e.g. a first heat exchanger for indirect heat exchange against urea solution that needs to be heated, e.g. for water evaporation, and a second heat exchanger against cooling water. The second MP decomposer and the second MP carbamate condenser are preferably operated at substantially the same pressure. A higher condensation temperature is in such embodiments desired for the first heat exchanger.

The carbamate solution is recycled, directly or indirectly, to the HP synthesis section, e.g. to the HPCC of a thermal stripping plant, in particular to the process medium side of such a HPCC, e.g. the tube side of a kettle-type HPCC. This recycle typically involves pumping of the carbamate solution using a HP carbamate pump.

In an embodiment, the carbamate solution formed in the second MP carbamate condenser is pumped to the HP section using the carbamate pump of the first recovery section. For example, the carbamate solution formed in the second MP carbamate condenser is supplied to the MP separation column, and the outlet for carbamate solution of the MP separation column is connected (for liquid flow) directly or indirectly to an inlet of the HP carbamate pump of the first recovery section. This example embodiment is less preferred since the carbamate solution formed in the second MP carbamate condenser then becomes saturated with ammonia.

More preferably, the carbamate solution formed in the second MP carbamate condenser is pumped to the HP synthesis section using a dedicated pump, which pump is separate from the pump used to transport carbamate solution from the first MP carbamate condenser to the HP synthesis section. Preferably, the carbamate solution formed in the second MP carbamate condenser does not flow through the MP separation column. This provides the advantage that the carbamate solution does not take up $NH_3$ in said separation column such that the volume of the stream to be pumped by the additional pump is relatively small. The part of the $NH_3$ feed that is supplied to the first MP recovery section that is pumped by the ammonia pump is therefore relatively large, which is advantageous to reduce the specific amount of water recycled into the HP section.

The second MP recovery section further preferably comprises an inlet for a $CO_2$ feed gas stream, such that MP $CO_2$ feed is supplied directly or indirectly to the second MP carbamate condenser where it is subjected to condensation with ammonia (originating from the second stream, e.g. from the second MP decomposer) to form a carbamate solution.

Advantageously, in this way part of the $CO_2$ feed can be supplied at medium pressure and is pumped to high pressure as carbamate solution. Therefore, in case of a revamp, the existing HP $CO_2$ compressor (typically present in the existing urea plant for providing HP $CO_2$ gaseous feed to the HP synthesis section) does not need to be modified. In case of a grassroots plant, the HP $CO_2$ compressor can be relatively small. A HP $CO_2$ compressor usually incurs large capital expenditure compared to a carbamate pump and a MP $CO_2$ compressor. In some embodiments, the plant comprises a MP $CO_2$ compressor to compress $CO_2$ feed to medium pressure, in particular to a pressure above the operating pressure of the second MP carbamate condenser. In some embodiments, MP $CO_2$ feed is obtained from an intermediate stage of a multi-stage HP $CO_2$ compressor.

Usually, $CO_2$ is available at battery limit at low pressure (e.g. 1-5 bar abs.) from an ammonia plant (in particular, from the syn gas plant). The MP $CO_2$ feed is e.g. compressed to MP using a MP $CO_2$ compressor or by extracting $CO_2$ feed from an intermediate stage of the HP $CO_2$ compressor. In some embodiments, no passivation oxygen is added to the MP $CO_2$ feed and/or no oxygen for a hydrogen convertor unit is added to the MP $CO_2$ feed. This advantageously allows for low inert contents in the second MP carbamate condenser, which is particularly advantageous in embodiments wherein the second MPCC comprises a first heat exchanger for indirect heat exchange against urea solution that needs to be heated.

In a preferred embodiment, the MP $CO_2$ feed is supplied to a MP $CO_2$ stripper comprised in the second MP recovery section. In this MP stripper preferably the urea solution from the MP decomposer is subjected to stripping (counter-current contact with the $CO_2$ gas flow) to give a vapor stream and a MP stripped solution. The stripping in the MP $CO_2$ stripper is preferably adiabatic. The MP $CO_2$ stripper comprises for instance a packed bed adapted for counter-current contacting of gas and liquid.

The urea solution at the liquid outlet of the MP $CO_2$ stripper typically has a lower N/C ratio than the urea solution at the liquid inlet of the MP $CO_2$ stripper. Thereby the urea solution at the outlet is more suitable for processing in a downstream LP recovery section.

The vapor stream from the MP $CO_2$ stripper is sent to the second MP carbamate condenser.

Supplying MP $CO_2$ feed to the second MP carbamate condenser, optionally through the MP $CO_2$ stripper, provides the advantage that the carbamate solution formed in the second MP carbamate condenser has a relatively low N/C ratio and therefore, for a fixed amount of carbamate, a lower volume. The lower volume is advantageous for pumping the MP carbamate solution. The adiabatic flash can be adjusted so as to have sufficient $NH_3$ in the second MP carbamate condenser.

The first stream has for instance an N/C ratio in the range 3.3-3.6 at the reactor outlet and at the outlet of the HP separator.

The urea solution at the outlet of the HP thermal stripper contains e.g. 23-25 wt. % $NH_3$ (both free and as carbamate) and 6-7 wt. % $CO_2$ (both free and as carbamate).

The carbamate solution from the first MP carbamate condenser has an N/C ratio of e.g. 3 to 4, or from 3.50 to 4.50

In an example embodiment, the liquid obtained from the bottom of the separation column, prior to mixing with carbamate solution from the second MP recovery section, contains 50-60 mol %, e.g. 56 mol %, $NH_3$ (both free and as carbamate), 10-20 mol. %, e.g. 14 mol %, $CO_2$ (both free and as carbamate) and 25-35 mol %, e.g. 29 mol %, $H_2O$. The high N/C ratio makes a high water content necessary.

Preferably, the carbamate solution from the second MP carbamate condenser has an N/C ratio of 2.10 to 2.50, e.g. 2.20 to 2.40.

For example, the carbamate solution from the second MP carbamate condenser contains 50-60 mol %, e.g. 55 mol. % $NH_3$ (both free and as carbamate), 20-25, e.g. 22 mol. %

$CO_2$ (both free and as carbamate), and 20-25 mol %, e.g. 23 mol % $H_2O$. The solution e.g. has a pressure of 17-18 bar.

Preferably, the carbamate solution from the first MP recovery section, as received by the HP section (i.e. at the outlet of the HP carbamate pump), has a water content of 23-27 wt. %, and the carbamate solution from the second MP recovery section, as received by the HP section has a water content of 18-22 wt. %, for instance wt. %.

Preferably the carbamate solution from the first MP carbamate condenser has a water content of 23-27 wt. %, e.g. 25 wt. %, and the carbamate solution from the second MP carbamate condenser has a water content of 18-22 wt. %, for instance 20 wt. %. The carbamate solution from the second MP carbamate condenser therefore has a better quality with the design of the present invention, in particular by virtue of the high pressure separation step and/or the preferred MP adiabatic flash.

The purified urea solution from the first MP recovery section and from the second MP recovery section are both sent to a LP recovery section of the urea plant, e.g. to two separate LP recovery sections or to the same LP recovery section. The one or more LP recovery sections typically comprise a LP decomposer and a LP carbamate condenser. The LP carbamate solution from the LP carbamate condenser is e.g. supplied to the first and/or second MP carbamate condenser.

Figure 1:
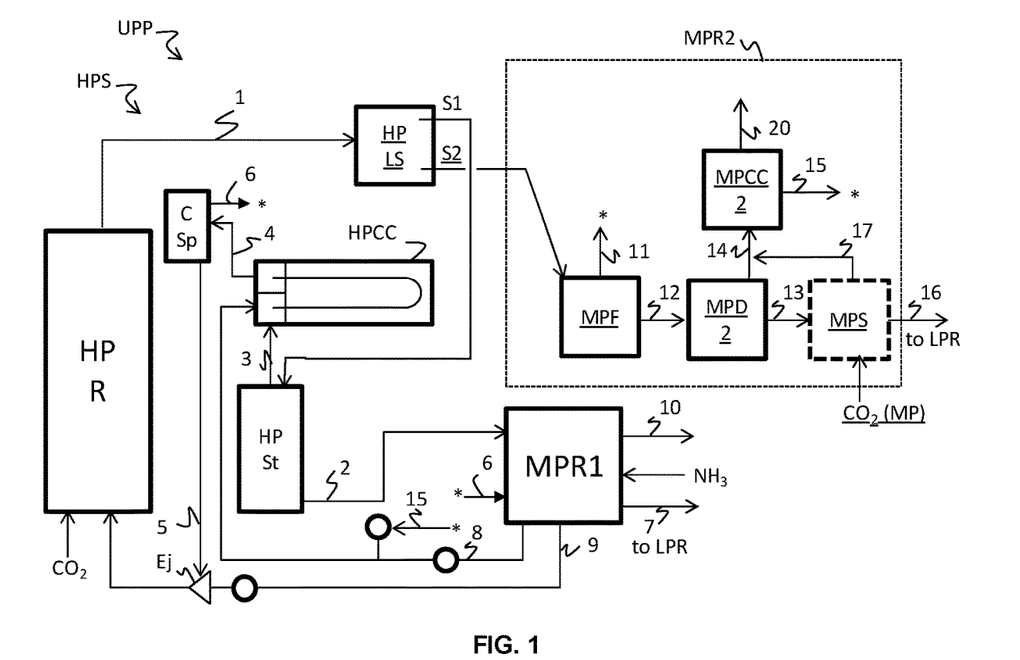
FIG. 1 schematically illustrates an example process scheme according to the invention.

FIG. 1 schematically illustrates an example process scheme according to the invention which does not limit the invention and does not limit the claims. In the following description, reference numbers as shown in FIG. 1 are used merely for convenience and without limiting the invention in any way.

The inventive urea production process is generally carried out in a urea production plant (UPP) of the thermal stripping type. The plant comprises a high pressure (HP) synthesis section (HPS) and a first and a second medium pressure (MP) recovery section (MPR1, MPR2). The first and second MP recovery section receive a urea-comprising stream from the HP synthesis section and yield a MP urea solution which is typically further processed in a LP recovery section to give a LP urea solution which is for instance further concentrated in an evaporation section to form a urea melt. The urea melt is often sent to a finishing section where solid urea product is formed, e.g. a granulator or prilling tower. The evaporation section is used for water removal, the resulting water vapor is condensed and the condensate is typically treated in a waste water treatment section (WWT) comprising a hydrolyser and a desorber. The WWT typically has relatively high energy consumption.

Other uses of the urea melt and of the urea solution are also possible.

The HP synthesis section comprises a HP reaction zone (HPR), a HP stripper of the thermal stripping type (HPSt), and a HP carbamate condenser (HPCC).

The HP reaction zone (HPR) is e.g. provided by one or more HP urea reactors. If two or more HP urea reactors are used, these are e.g. arranged in parallel or in series. The one or more HP reactors are typically vertical bubbling columns with trays. In the present invention, the reactor is e.g. operated at 180-200° C., e.g. 185-195° C., and/or at a pressure of at least 140 bar, e.g. 140-160 bar or 150-160 bar. The reactor is operated e.g. with an N/C ratio in the range of 3.00 to 3.40, e.g. in the range of 3.1 to 3.2.

The urea production process for instance involves supplying oxygen ($O_2$) for passivation purposes into the HP reaction zone (HPR), for example in an amount of at least 0.010 vol. % based on fresh $CO_2$ feed, e.g. by introducing air in an amount of at least 0.10 vol % and typically less than 1.0 vol. % relative to fresh $CO_2$ feed. The passivation air or oxygen is e.g. supplied as part of the $CO_2$ feed. The passivation air or oxygen is e.g. supplied directly to the HP urea reactor.

The HP stripper (HPSt) has an outlet for stripped urea solution (2) connected to the first MP recovery section (MPR1) and an outlet for gas (3) connected to the HP carbamate condenser (HPCC). The HP stripper (HPSt) is typically a vertical shell-and-tube heat exchanger of the falling-film type with urea solution to be stripped in the tubes, with an outlet for a mixed gas stream at the top connected to the HP carbamate condenser (HPCC) and with an outlet for stripped urea solution at the bottom. The HP stripper is preferably configured as thermal stripper. The tubes of the stripper are without limitation e.g. bimetallic tubes, or comprise e.g. Ti and/or Zr, or are e.g. made of suitable stainless steel, such as for example a duplex ferritic-austenitic stainless steel, for instance a duplex stainless steel as described in WO 2017/014632.

In the process of the invention, the thermal stripper is operated at e.g. 200-210° C., these temperatures indicating the urea solution outlet temperature.

The HP carbamate condenser (HPCC) is preferably a shell-and-tube heat exchanger, more preferably a heat exchanger with a horizontal U-shaped tube bundle. For example the HPCC is configured for operation with liquid as continuous phase on the process side. The HP carbamate condenser is preferably of the kettle-type with a horizontal U-shaped tube bundle, having an inlet for receiving gas to be condensed inside the tubes and an inlet for receiving cooling fluid in the shell. Other types of HP carbamate condenser are also possible, such as with a vertical U-shaped tube bundle, or with a horizontal U-shaped tube bundle and with an inlet for receiving gas to be condensed in the shell and an inlet for receiving cooling fluid in the tubes.

Preferably the HPCC additionally receives medium pressure carbamate solution from the first MP recovery section in the process side, such as in the tubes for a kettle-type condenser.

In some embodiments, the HP process fluid stream (4) from the HPCC contains carbamate solution and inerts and is supplied to a carbamate separator (CSp) operated at high pressure and configured for gas/liquid separation to give a liquid stream (5) and a gas stream (6). The liquid carbamate stream (5) is supplied to the reactor, typically using an ammonia-driven ejector (Ej). The gas (6) from the carbamate separator (CSp) contains inerts and ammonia and is supplied preferably to the first MP recovery section, e.g. to a bottom part of a MP decomposer. Supplying the gas (6) to the first MP recovery section (MPR1) is particularly advantageous in embodiments wherein the MP flash unit (MPF) receives degassed urea solution.

In the invention, the HP synthesis section further comprises a separator (HPLS), in particular a high pressure separator, more in particular a high pressure liquid separator. The separator is operated at high pressure. The separator is for instance a dedicated unit or is arranged inside a reactor vessel. If two or more reactors are used in series, the separator is preferably arranged in the most downstream reactor. A separator provided as a dedicated unit, is preferably arranged downstream of the reactor. The separator is preferably arranged at a downstream part of the reaction zone. The separator preferably receives reaction mixture wherein the conversion (urea formation) is already at least 90% completed relative to the total conversion achieved in the HP synthesis section. The reaction mixture at the inlet of the separator comprises e.g. at least 30 wt. % urea, such as 30-35 wt. % urea. Preferably, no $NH_3$ and/or no gaseous components are removed from the reaction mixture in the reaction zone prior to the separation in the HP separator.

The inventive urea production process involves separating the reaction mixture from the reaction zone (HPR) at high pressure in said separator (HPLS) into a first stream, e.g. an ammonia-rich first stream (S1), and a second stream (S2). The first and second stream both contain a liquid phase; this liquid phase contains urea. The ammonia-rich first stream (S1) preferably has a lower gravimetric density than the second stream (S2), at the separation. The separation can be based for instance on gravimetric density separation. The first stream (S1) has for instance a higher concentration of ammonia than the second stream (S2) based on the total volume of the two streams (including gas and liquid in case of two phase fluid streams). In particular, the second stream is optionally substantially free of gas, such that the gas fraction gaseous components of the reaction mixture end up in the first stream; these gaseous components can be rich in ammonia. Accordingly, the first stream (S1) comprises inerts and in particular the first stream (S1) has a higher content (wt. %) of inert components than the second stream (S2). Inert components in urea plant include $H_2$ and $O_2$. For instance, the first stream (S1) has a higher content (wt. %) of $H_2$ and a higher content of 02 than the second stream (S2). The inert components included in the first stream (S1) pass through the HP stripper (HPSt) and through the HP carbamate condenser (HPCC) thereby contributing to passivation of said HP units and preventing corrosion in said units.

In the process, the ammonia-rich first stream (S1) is supplied at least in part, such as entirely, to the HP stripper of the thermal stripping type. The second stream (S2) is supplied at least in part, such as entirely, the second MP recovery section (MPR2).

In a preferred embodiment, the HP separator is arranged at a downstream end of the reaction zone. This provides the advantage that the liquid phases of the first and the second stream have a substantially identical composition, in particular can have substantially the same composition in the flow connections (pipes) for transporting the first stream at least in part to the thermal stripper and for transporting the second stream to the second MP recovery section.

Preferably the process involves determining the N/C ratio of the second stream.

Preferably the process involves determining the N/C ratio of the degassed stream from the HP separator.

Determining the N/C ratio is advantageously in particular simple in preferred embodiments wherein the second stream consists of degassed liquid. Very advantageously in these embodiments with a degassed second stream consists of liquid, instead of a two-phase gas/liquid fluid stream, and the N/C ratio can accordingly be conveniently measured. In this way, very advantageously, the N/C ratio of the liquid phase comprised in the first stream can also be determined as it is substantially the same as the measured N/C ratio of the second stream. This can be used for better controlling the operation of the synthesis section, such as the reactor and the thermal stripper, and the first MP recovery section; such as during start-up of the plant. Information about the N/C ratio in the liquid phase is useful because the urea formation reaction takes place only in the liquid phase in the reactor.

Preferably the plant comprises an N/C meter in the flow line for the degassed stream, preferably in the flow line for the degassed second stream to the MP recovery section. Preferably a small part of the HP degassed liquid stream is drawn off and supplied to the N/C meter.

Continuous N/C meters for liquid urea reactor effluent are known in the art and use e.g. the relationship (correlation) between liquid density and N/C ratio e.g. at fixed temperature and pressure. The N/C meter is for example based on measuring the liquid density using e.g. a Coriolis density measurement, a nucleonic density gauge, or e.g. vibrating element technology to measure liquid density. Other methods can also be employed. Information about the N/C ratio of the first stream supplied to the thermal stripper is in particular useful in the inventive process wherein the operation of the first and second recovery section, e.g. the preferred adiabatic flash, provides for increased flexibility for optimizing the urea yield.

By measuring the N/C ratio, the $NH_3$ supply and/or $CO_2$ supply to the synthesis section can be adjusted so as to obtain optimum yield, preferably by adjusting the $NH_3$ recycle flow rate. Preferably the process involves adjusting the $NH_3$ supply and/or $CO_2$ supply to the HP synthesis section, in particular the $NH_3$ recycle stream flow rate, depending on the measured N/C ratio.

The installation of the N/C meter ensures a stable plant operation with lower energy consumption and lower ammonia emission, especially because the two MP recovery sections typically generate carbamate solutions with different N/C ratios.

The first MP recovery section (MPR1) generally yields a MP urea solution (7) comprising e.g. 55-65 wt. % urea, e.g. 60-65 wt. % urea, a carbamate recycle stream (8) and a separate liquid ammonia recycle stream (9), as well as a gaseous stream comprising inerts (10).

Preferably, first MP recovery section (MPR1) comprises a first MP decomposer (MPD-1), a first MP carbamate condenser (MPCC-1), and an ammonia condenser (AC), as well as preferably a MP separation column (MPSC) and an ammonia receiver (AR).

Figure 2:
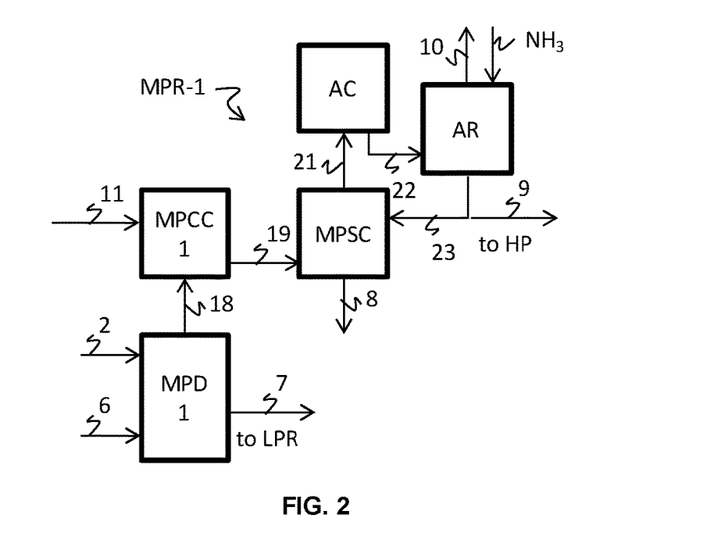
FIG. 2 schematically illustrates an example process scheme of a second medium pressure recovery section used in the invention.

FIG. 2 schematically illustrates an example first MP recovery section (MPR1). The first MP decomposer (MPD-1) receives the expanded stripped urea solution (2) and uses heating to decompose carbamate contained in stripped urea solution, as well as to remove $NH_3$. For instance, the decomposer comprises a solution inlet (2) at the top and gas outlet (18) at the top, a packing, and a shell-and-tube heat exchanging part, and a solution outlet (7) at the bottom, and optionally an inlet (6), preferably at the bottom, for receiving gas from the HP carbamate separator (CSp).

The first MP carbamate condenser (MPCC-1) has an inlet for receiving gas (18) from the MP decomposer (MPD-1) and is configured for at least in part condensing $CO_2$ and $NH_3$ comprised in said gas into carbamate solution, typically after receiving also some carbamate solution from a LP recovery section. The relatively high water content of LP carbamate solution can be used to avoid crystallization of the MP condensate. The MP carbamate solution (8) formed in the first MP carbamate condenser (MPCC-1) is generally supplied directly or indirectly to the HP synthesis section as carbamate recycle solution using a pump.

The first MP carbamate condenser (MPCC-1) highly preferably also receives the gas stream (11) from the adiabatic flash. In this way, components of that gas stream (11) which are not condensed in MPCC-1, such as excess $NH_3$, are advantageously purified in the separation column (MPSC) and can be condensed as relatively pure liquid ammonia in the ammonia condenser (AC), e.g. MP ammonia condenser. The ammonia condensate (22) from the ammonia condenser (AC) contains (almost) no carbamate. The ammonia condensate (22) accordingly may have low water content. The ammonia condensate (22) is preferably substantially pure ammonia.

The condensation can be carried out using one or more heat exchanging units and using as cooling fluid e.g. cooling water and/or urea solution that needs to be heated. The first MP carbamate condenser (MPCC-1) is e.g. provided, as a MP condenser/pre-evaporator for indirect heat exchange against urea solution to be heated, optionally with a further downstream MP condenser for condensing at least a part of the non-condensed gases from the first MP carbamate condenser (MPCC-1). The downstream MP condenser operates e.g. with cooling water. The MP condenser/pre-evaporator is for instance a shell-and-tube heat exchanger with gas to be condensed in the shell and urea solution to be heated in the tubes. The urea solution to be heated originates e.g. from an LP recovery section of the plant and process.

Preferably, the MP condensate (19) is supplied to an ammonia-carbamate separation column (MPSC) together with uncondensed gas, and the uncondensed gas is for instance refluxed with relatively cold liquid $NH_3$ feed in the column in order to remove $CO_2$ from the gas. The column (MPSC) is for instance used as a distillation column.

In a preferred embodiment, the MP condensate (19) is supplied to the bottom of the column and heated, and feed liquid $NH_3$ is supplied to the top of the column Preferably the column comprises trays. Preferably, additionally an aqueous stream is supplied just below the top of the column. Advantageously, the gas stream (21) from the top of the separation column contains only $NH_3$ and inerts. This gas stream (21) is preferably supplied to the ammonia condenser (AC). The bottom product of the ammonia-carbamate separation column (MPSC) is the MP carbamate solution (8) and contains relatively much $NH_3$ and water.

The non-condensed gas stream from the first MP carbamate condenser (MPCC-1) is preferably after purification to purer ammonia gas, supplied to a (first) ammonia condenser (AC), which is a heat exchanger preferably using cooling water as cooling fluid. The ammonia condenser is preferably operated at a temperature in the range of 20 to 50° C.

The condensed ammonia (9) is recycled to the HP synthesis section, preferably after the inert gaseous components (10) being separated from the liquid in an ammonia receiver (AR) wherein liquid $NH_3$ feed is also received. The liquid ammonia from the ammonia receiver (AR) is in part (9) pumped to the HP section and in part (23) used in the MP separation column (MPSC).

The gas stream (10) is for instance supplied to a scrubber (not shown) where it is scrubbed with an aqueous stream, e.g. steam condensate, from which liquid is typically recycled to the HP synthesis section, e.g. by supplying it to the ammonia-carbamate separation column (MPSC).

The WWT section comprises e.g. a hydrolyser and desorber. Especially in embodiments wherein the MP flashing unit receives degassed urea solution, the amount of inerts in the gas stream (10) can be relatively low and accordingly the energy consumption of the WWT section can advantageously be relatively low.

The second MP recovery section (MPR2) comprises a second MP decomposer (MPD2) and a second MP carbamate condenser (MPCC2). An example second MP recovery section is illustrated in FIG. 1.

Preferably the process involves expanding the preferably degassed second stream (S2) from high pressure to medium pressure in the second MP recovery section in the preferred MP adiabatic flashing step (MPF) as discussed to give a gaseous stream (11) (flash vapor) and a flashed MP urea solution (12). Preferably the MP flash is carried out at a pressure in the range of 25 to 40 bar. Preferably the second MP decomposer operates at a pressure slightly lower than the MP flash unit, e.g. 1 bar lower. Preferably the plant comprises an expansion valve between the MP adiabatic flash unit and the second MP decomposer.

The preferably flashed MP urea solution (12) is subjected to decomposition of ammonium carbamate in said second MP decomposer (MPD2) to give treated urea solution (13) and a gas stream (14). The second MP decomposer (MPD2) is typically a heat exchanger for indirect heat exchange with steam. The gas stream (14) is subjected to condensation in second MP carbamate condenser (MPCC2) to give a gas stream (20) a carbamate solution (15) which is recycled to the HP section (HPS). Any non-condensed gases (20) can be supplied e.g. to an LP carbamate condenser comprises in an LP recovery section. Particularly advantages the non-condensed gases (20) have low inert content such that they can be condensed and scrubbed in the LP recovery section to give an LP carbamate stream with low water content that is recycled directly or indirectly to the HP synthesis section. The carbamate solution (15) from the second MP carbamate condenser (MPCC2) is for instance pumped to the HP carbamate condenser using preferably a dedicated carbamate pump, for instance if MPCC-2 operates at higher pressure than MPCC-1.

Preferably, the plant comprises, as separate pumps, an ammonia HP pump, a carbamate pump of the first MP recovery section, and a carbamate pump of the second MP recovery section, for pumping these three streams separately to the HP section. This in particular allows the streams to have different temperatures and/or different pressures in the MP range, which contributes advantageously to lower water content of the recycle stream (15).

In other possible embodiments, the carbamate solution (15) bypasses the MP separation column (MPSC) and is supplied to the carbamate pump used in the first recovery section (MPR1) for pumping the carbamate solution (8) to the HP section.

Preferably the second MP recovery section (MPR2) further comprises a MP $CO_2$ stripper (MPS). Preferably in this stripper the urea solution (13) from the second MP decomposer (MPD2) is stripped/contacted in counter-current flow with MP $CO_2$ feed in said MP $CO_2$ stripper (MPS) to give further treated urea solution (16) and a gas stream (17). The gas stream (17) is subjected to condensation to give carbamate solution in said second MP carbamate condenser (MPCC2). Thereby a desirable low N/C ratio of the carbamate solution (15) is obtained.

The invention also pertains to a urea plant (urea production plant) which preferably suitable for the inventive processes. Preferences for and details of the plant, units and connections as discussed herein in connection with the urea production process apply also for the inventive plant. The plant comprises a high pressure synthesis section comprising a reaction zone, a thermal stripper, and a carbamate condenser. The reaction zone is for instance provides as one or more reactors, in particular one or more vertical reactors. The vertical urea reactors comprise e.g. one or more inlets at the bottom and an outlet for the first and the second stream at an upper part of the reactor. In case of two or more reactors, these are e.g. arranged in series, although they can also be arranged in parallel. The plant further comprises a first medium pressure recovery section having an inlet connected to an outlet for stripped urea solution of said thermal stripper. The high pressure synthesis section comprises a high pressure separator configured for separating a high pressure reaction mixture from the reaction zone into a first stream and a second stream. The separator is typically configured such that the first stream and the second stream both contain a liquid phase containing urea and the first stream (S1) optionally has a lower gravimetric density than the second stream (S2). Furthermore, the high pressure separator has a first outlet for the first stream connected to an inlet of said thermal stripper, and a second outlet for the second stream connected to a second medium pressure recovery section. Details for the first and second medium pressure recovery section are the same as discussed in connection with the process. The separator has for instance a funnel design, with a wide opening at an upper part of the funnel and a narrow opening at a bottom part, with the narrow opening connected to the outlet for the second stream. Herein, the terms upper and lower are used as defined with respect to gravity. The separator is for instance arranged in an upper part of a second vertical reactor which is arranged in series downstream of a first vertical reactor. The second reactor has for instance an inlet connected to an outlet for reaction mixture of the first reactor. The second reactor has for instance a smaller volume than the first reactor.

Details for the first and second medium pressure recovery section as discussed herein for the urea production process apply equally for the inventive plant.

In a preferred embodiment, the urea plant comprises an N/C meter for measuring the N/C ratio of the fluid, in particular liquid, in the flow line for the second stream from the high pressure separator to the medium pressure recovery section, more preferably a continuous N/C meter. The N/C meter is for example selected from the group consisting of Coriolis density measurement devices, nucleonic density gauges and vibrating element technology devices to measure liquid density. The plant for example also comprises a flow meter to measure the flow rate in the flow line for the second stream.

In case of a grassroots plant, the HP stripper can be relatively small for the plant capacity by virtue of the second MP recovery section.

The invention also pertains to a revamping method. Preferably, the method pertains to a method of modifying an existing urea plant of the thermal stripping type. Preferably, the revamp is used to increase the capacity of the plant and preferably the method involves a step of increasing the reactor volume of the high pressure synthesis section, for instance by adding an additional reactor.

The existing plant is modified into an inventive plant as described herein. The method involves a step of adding a HP separator as described and by adding a second MP recovery section as described, in particular by adding the preferred adiabatic flash unit connected by a flow line to the outlet for the second stream of the added HP separator, a MP decomposer, MP carbamate condenser, and optionally a MP stripper. Also added is a MP $CO_2$ feed inlet connected to the second MP recovery section to supply MP $CO_2$ directly or indirectly to the MP carbamate condenser, preferably through a MP $CO_2$ stripper.

An example revamping method is schematically illustrated in FIG. 1, wherein the revamp method comprises adding the underlined units to the existing plant (added units: HPLS, MPF, MPD2, MPCC2, and MPS).

Preferably an N/C meter is added in the flow line for the second stream. The N/C meter may be used, for instance, for adjusting the operation of the added sections in the modified plant.

Preferably in the method a gas flow line for the gaseous stream from the MP adiabatic flashing unit to the first medium pressure (MP) recovery section is also added, more preferably to the first MP carbamate condenser.

In a preferred revamping method, the method involves adding an additional (second) urea reactor downstream of an existing first urea reactor, receiving reaction mixture from the top of the first reactor. The reactors are hence arranged in series. Preferably, the exiting first reactor has only one outlet, used for both gas and liquid, connected to the thermal stripper. The existing first reactor is for instance a vertical reactor having only one outlet located at the top.

Preferably, the high pressure separator added as part of the revamp is arranged inside said additional reactor. The second/additional urea reactor preferably comprises the HP separator at an upper part. The second urea reactor accordingly preferably has an outlet for the first stream and a separate outlet for the second stream. Using two vertical reactors in series allows for a longer residence time and higher conversion of carbamate to urea. The outlet of the first reactor is preferably at the top and connected to an inlet of the second reactor at a bottom part of the second reactor. The first and second reactor are preferably installed at or near ground level. The bottom of the second reactor is preferably arranged below the top of the first reactor.

Advantageously, the revamp does not require extensive modifications of the HP synthesis section and the first MP recovery section of the existing plant, while the modified plant can have a significantly increased capacity.

The plant of the invention and the urea production process of the invention can be used for grassroots plants as well as for a revamp of existing plants.

Figure 3:
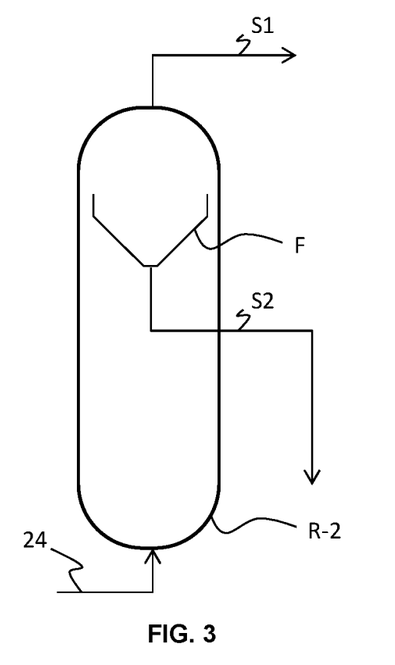
FIG. 3 schematically illustrates an example high pressure separator used in the invention.

FIG. 3 schematically illustrates an example second downstream vertical urea reactor (R-2) which is added in a revamp of an existing plant of the thermal stripping type. Generally in preferred embodiments of the revamping method according to the invention, the second reactor is added between the vertical urea reactor of the existing plant and the thermal stripper and has an inlet at the bottom for reaction mixture (24) received from the top outlet of the upstream first reactor. The second reactor has an outlet for the first stream (S1) at the top. In preferred embodiments of the inventive urea production process, the added second reactor is completely filled and no liquid level (gas-liquid interface) is present in the reactor.

The reactor comprises the separator which has a funnel design. The separator comprises a funnel (F) with a bottom and a top, with the narrow opening at the bottom and the wide opening at the top. The bottom opening is connected to the outlet for the second stream (S2), in particular to a downcomer. The funnel comprises e.g. a ring at the top and a frustro-conical segment. The use of a wide funnel provides for low liquid velocity contributing to degassing of the second stream.

Figure 4:
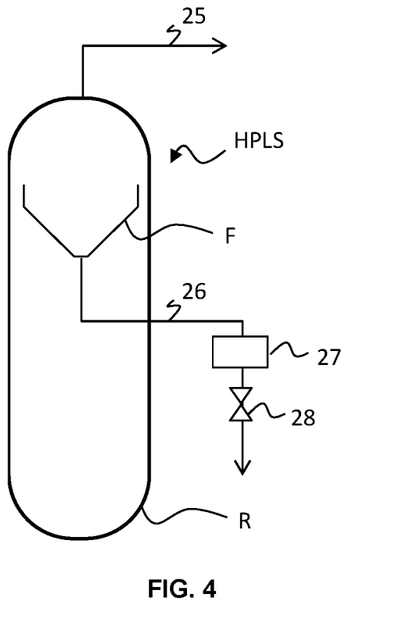
FIG. 4 schematically illustrates an example high pressure separator used in embodiments of the invention.

FIG. 4 schematically illustrates an example high pressure separator (HPLS) in a urea reactor (R), for example constructed as a funnel (F) with a bottom and a top, with the narrow opening at the bottom and the wide opening at the top. The bottom opening of the funnel is connected to an outlet for a degassed liquid stream (26) which is preferably the second stream (S2) supplied to the second MP recovery section but alternatively can also be the first stream (S1) supplied to the thermal stripper. The flow line for the degassed stream comprises an N/C meter (27) an expansion valve (28) for expanding to MP. The reactor also has an outlet (25) at the top for a gas/liquid mixture which preferably is supplied as the first stream to the thermal stripper but alternatively is supplied as the second stream to the second MP recovery section.

As used herein, the N/C ratio refers, as is customary in the field, for liquid streams to the molar ratio of $NH_3$ to $CO_2$, in particular in the reaction zone based on the theoretical initial mixture. For gaseous streams the N/C ratio indicates the molar ratio $NH_3$ to $CO_2$.

As used herein, high pressure (HP) is at least 100 bara, e.g. 110 to 160 bara, in particular 140-160 bar; medium pressure (MP) is e.g. 10 to 60 bara, such as 20-60 bara, and low pressure (LP) is e.g. 4 to 10 bara; these pressure ranges are for process solutions and not necessarily the same for steam and heating fluids. The abbreviation "bara" means bar absolute. Pressures as used herein are absolute pressure unless stated otherwise.

In conclusion, the invention pertains to a urea production plant and process using a thermal stripper, wherein the reaction mixture is separated in two parts, wherein the first part is supplied at least in part, such as entirely, to the thermal stripper and the second part at least in part, such as entirely, bypasses the thermal stripper and is supplied to a medium pressure recovery section. The first and second part optionally have a different composition.

The invention claimed is:

1. A urea production process carried out in a urea production plant, the plant comprising a high pressure (HP) synthesis section and a first and a second medium pressure (MP) recovery section,
    wherein the HP synthesis section comprises a HP reaction zone, a HP thermal stripper, a HP carbamate condenser, and a separator, wherein the HP thermal stripper has an outlet for a stripped urea solution connected to the first MP recovery section and an outlet for a gas connected to the HP carbamate condenser,
    the process comprising:
        separating a reaction mixture from the HP reaction zone at high pressure in said separator into a first stream and a second stream, wherein the first stream and the second stream both contain a liquid phase containing urea;
        supplying the first stream at least in part to the HP thermal stripper, and obtaining stripped urea solution from the HP thermal stripper; and
        supplying the second stream at least in part to the second medium pressure recovery section,
    wherein the first stream has a lower gravimetric density than the second stream and the first stream is an ammonia-rich first stream having a higher concentration of ammonia than the second stream.

2. The urea production process according to claim 1, wherein the process comprises:
    degassing the second stream in the separator to obtain a degassed second stream, wherein the degassed second stream has an N/C ratio;
    measuring the N/C ratio of the degassed second stream; and
    supplying the degassed second stream to the second MP recovery section bypassing the HP thermal stripper.

3. The urea production process according to claim 1, wherein the first MP recovery section comprises a first MP decomposer, a first MP carbamate condenser, a medium pressure separation column, and an ammonia condenser, wherein the process comprises:
    subjecting the stripped urea solution to decomposition in said first MP decomposer to give a MP urea solution and a gas stream,
    subjecting the gas stream to condensation in said first MP carbamate condenser,
    separating a stream from said first MP carbamate condenser in said medium pressure separation column into an MP carbamate solution and an ammonia-containing gas stream, and
    subjecting the ammonia-containing gas stream to condensation in said ammonia condenser to give an ammonia condensate stream.

4. The urea production process according to claim 1, wherein the HP reaction zone comprises said reaction mixture, wherein said reaction mixture in said HP reaction zone has an N/C ratio, wherein said N/C ratio of said reaction mixture in the HP reaction zone is greater than 3.0.

5. The urea production process according to claim 4, wherein said N/C ratio in the HP reaction zone is in the range 3.2-3.6.

6. The urea production process according to claim 4, wherein the HP reaction zone is operated at a pressure of at least 150 bar.

7. The urea production process according to claim 1, wherein the HP thermal stripper comprises a plurality of bimetallic tubes.

* * * * *